United States Patent
Behrens

(10) Patent No.: US 6,932,818 B2
(45) Date of Patent: Aug. 23, 2005

(54) INTRAMEDULLARY NAIL-BASED BONE FRACTURE TREATMENT

(76) Inventor: Alfred F. Behrens, One Harwood Dr., Madison, NJ (US) 07940-2710

(*) Notice: Subject to any disclaimer, the term of this patent is extended or adjusted under 35 U.S.C. 154(b) by 0 days.

(21) Appl. No.: 10/697,227

(22) Filed: Oct. 30, 2003

(65) Prior Publication Data

US 2005/0096656 A1 May 5, 2005

(51) Int. Cl.⁷ .............................................. A61B 17/72
(52) U.S. Cl. ...................................................... 606/64
(58) Field of Search ............................ 606/98, 96, 62, 606/64, 67, 60, 65

(56) References Cited

U.S. PATENT DOCUMENTS

| | | | |
|---|---|---|---|
| 2,812,761 A | | 11/1957 | Palkovitz |
| 3,996,931 A | * | 12/1976 | Callender, Jr. ............... 606/65 |
| 4,281,649 A | | 8/1981 | Derweduwen |
| 4,667,664 A | | 5/1987 | Taylor et al. |
| 4,733,654 A | * | 3/1988 | Marino ......................... 606/64 |
| 4,865,025 A | | 9/1989 | Buzzi et al. |
| 4,913,137 A | * | 4/1990 | Azer et al. .................... 606/64 |
| 5,176,681 A | | 1/1993 | Lawes et al. |
| 5,207,682 A | | 5/1993 | Cripe |
| 5,474,561 A | * | 12/1995 | Yao ............................... 606/98 |
| 5,766,174 A | | 6/1998 | Perry |
| 5,766,179 A | | 6/1998 | Faccioli et al. |
| 5,785,709 A | * | 7/1998 | Kummer et al. ............. 606/56 |
| 6,033,407 A | | 3/2000 | Behrens |
| 6,221,074 B1 | | 4/2001 | Cole et al. |
| 6,322,591 B1 | | 11/2001 | Ahrens |
| 6,702,815 B2 | * | 3/2004 | Kuntz ......................... 606/60 |
| 2001/0034523 A1 | | 10/2001 | Nelson |
| 2003/0069581 A1 | * | 4/2003 | Stinson et al. ................ 606/62 |
| 2003/0073999 A1 | * | 4/2003 | Putnam ....................... 606/62 |
| 2003/0114855 A1 | * | 6/2003 | Wahl et al. .................. 606/67 |

* cited by examiner

Primary Examiner—Eduardo C. Robert
Assistant Examiner—David Comstock
(74) Attorney, Agent, or Firm—Arthur Jacob

(57) ABSTRACT

A bone fracture located in one of the distal area and the proximal area of a long bone of the body is stabilized by inserting an intramedullary nail at a corresponding proximal end or distal end of the long bone, the intramedullary nail having a shank long enough to extend into the shaft of the long bone and reach the corresponding distal area or proximal area, and sockets located intermediate the ends of the shank for receiving anchoring pins extended transversely from the shaft of the long bone and to which a drill guide is coupled for enabling the drilling of holes in the long bone aligned with the fracture for insertion of stabilizing fasteners to stabilize the fracture. Insertion of the intramedullary nail at the appropriate end of the long bone and placement of the anchoring pins at the shaft of the long bone require only relatively small incisions and reduced dissection of soft tissue, by virtue of the location of the anchoring pins spaced longitudinally away from the proximal and distal areas of the long bone, so that blood loss is minimized and recovery is accelerated.

17 Claims, 10 Drawing Sheets

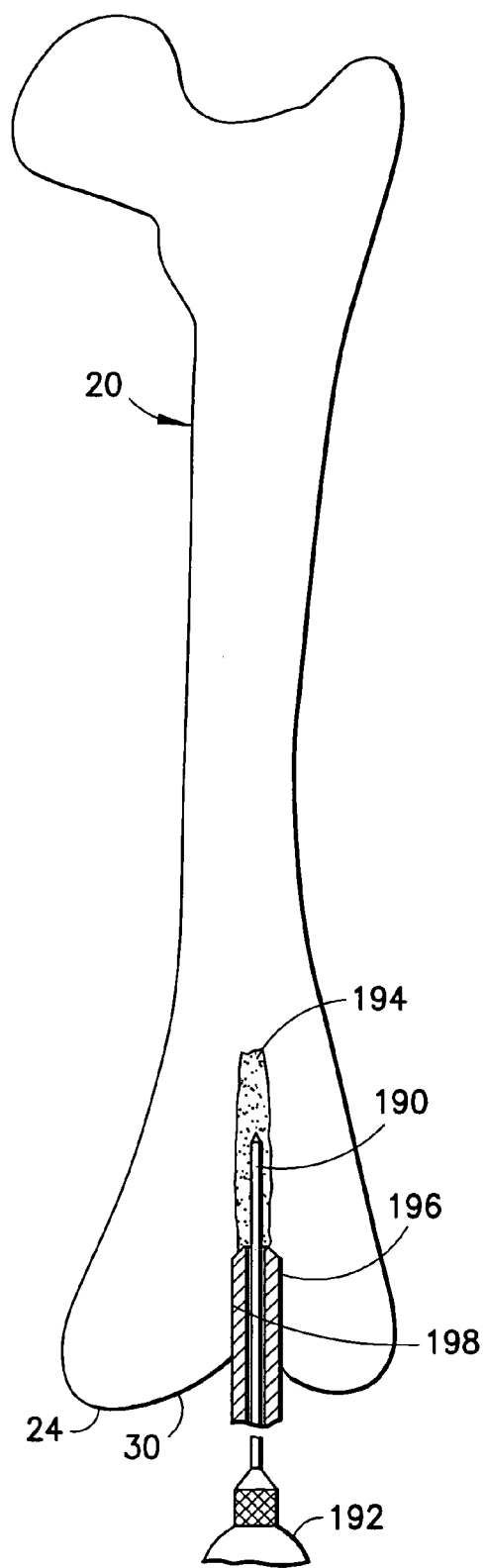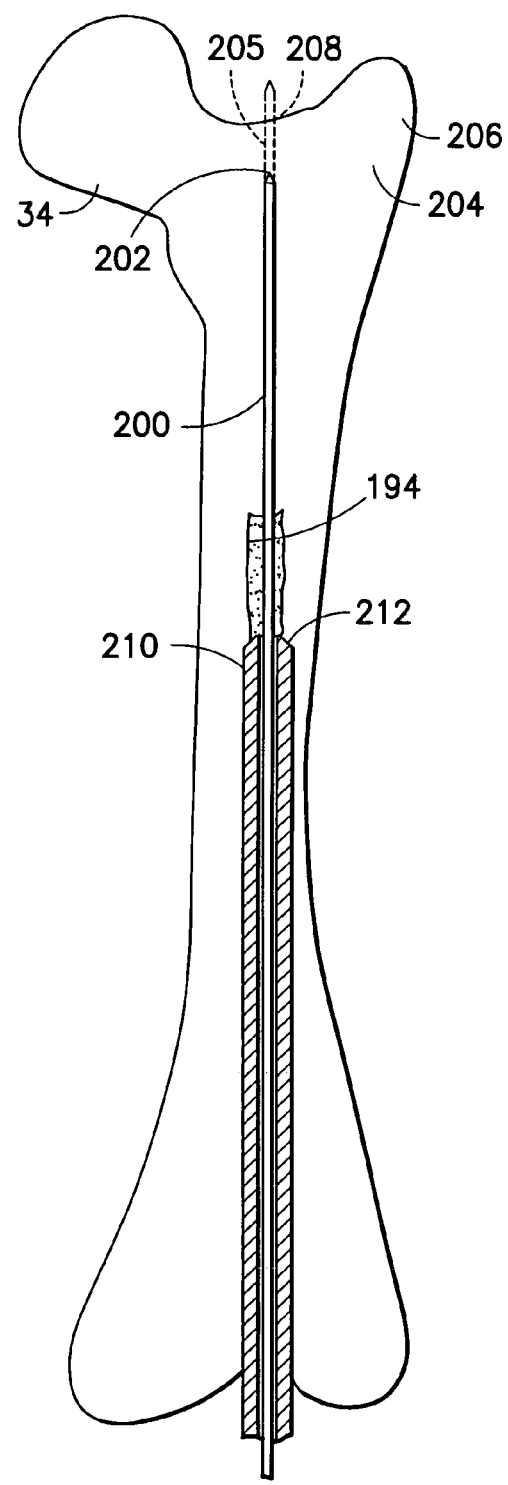
FIG.6
FIG.7

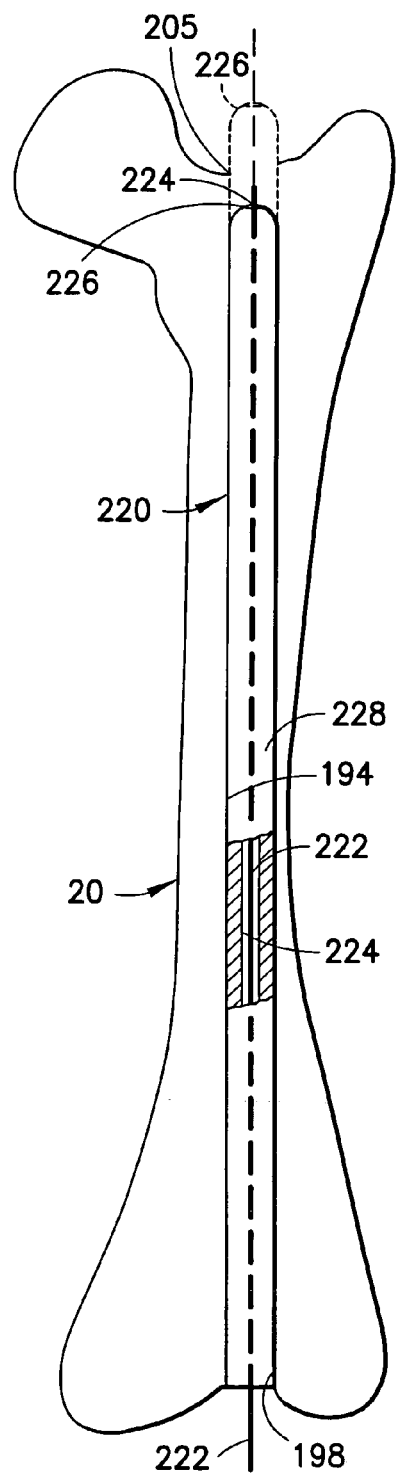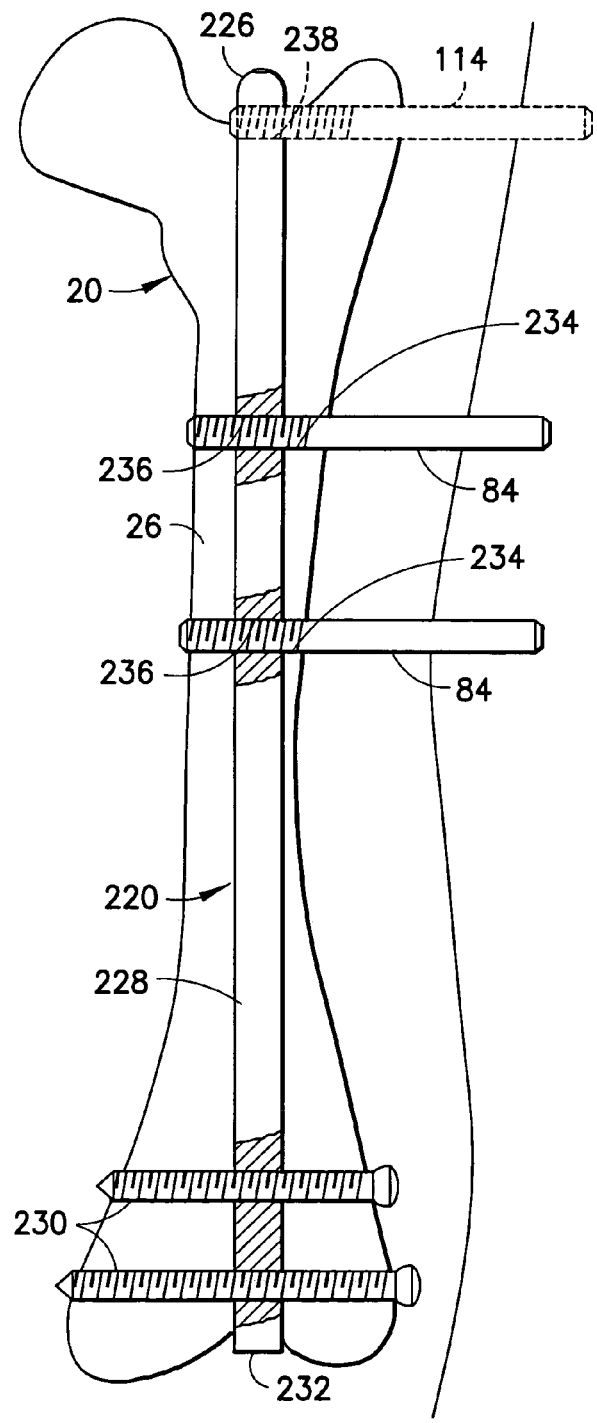
FIG.8
FIG.9

INTRAMEDULLARY NAIL-BASED BONE FRACTURE TREATMENT

The present invention relates generally to the treatment of bone fractures and pertains, more specifically, to the fixation of fractures in long bones in the body.

Currently, many long bone fractures, such as femoral hip fractures, that is, fractures of the femoral neck, intertrochanteric fractures and subtrochanteric fractures, are stabilized with screws, with plate-and-screw devices or with antegrade nails introduced through the hip area. Femoral neck fractures, if undisplaced, ordinarily are fixed with percutaneous screws, in a relatively benign procedure. However, where displacement and advanced osteopenia have occurred, the femoral head fragment is removed and a hemiarthroplasty usually is performed. The procedure is prone to complications and has experienced a relatively high mortality rate. Intertrochanteric fractures usually are stabilized with plate-and-screw devices or sometimes with antegrade trochanteric nails. These procedures require moderate incisions and usually consume one to two units of blood. Fractures of the subtrochanteric region are almost exclusively stabilized with antegrade nails. Such a procedure requires more extensive incisions and substantial soft tissue dissection. Thus, with the exception of the undisplaced femoral neck fracture, these fractures require major incisions and soft tissue dissection, causing substantial blood loss and postoperative morbidity and relatively high mortality. In addition, the treatment of such fractures often requires a prolonged hospital stay.

The present invention enables improved treatment of the above-described bone fractures, as well as other long bone fractures, through apparatus and procedures based upon the use of intramedullary nails having an extended length. In the past, retrograde nails have been used to manage some fractures of the femoral shaft and some supracondylar femoral fractures. These retrograde nails usually are inserted through a one to two inch long incision over the knee and rarely are advanced beyond the lesser trochanter (subtrochanteric area) of the femur. Because the use of a retrograde nail requires only a relatively small incision and no muscular dissection, blood loss is minimal and recovery is accelerated. Accordingly, the present invention attains several objects and advantages, some of which are summarized as follows: Provides apparatus and procedure enabling minimally invasive treatment of long bone fractures such as femoral hip fractures with concomitant minimal blood loss, shortened hospital stay and less discomfort, as well as reduced costs; allows the stabilization of long bone fractures, such as femoral hip fractures, without the necessity for excessive dissection of skin and muscle tissue around the hip; accomplishes the stabilization of long bone fractures such as femoral hip fractures with minimal to no radiographic support, enabling effective treatment at less elaborate and less expensive facilities; enables greater precision with increased ease for more effective fixation, especially in treating intertrochanteric and subtrochanteric hip fractures, without the need for major incisions in the hip area; permits the percutaneous fixation of undisplaced femoral neck fractures with diminished failure rates; reduces pain and recovery time; provides a surgeon with better options for treating long bone fractures such as femoral hip fractures.

The above objects and advantages, as well as further objects and advantages, are attained by the present invention which may be described briefly as a bone fracture treatment apparatus for stabilizing a fracture in a long bone of the body, the long bone having a proximal end, a distal end and a bone shaft extending between the proximal end and the distal end, the fracture being located adjacent one of the proximal end and the distal end, the apparatus comprising: an intramedullary nail insertable in the long bone through one of the proximal end and the distal end to extend longitudinally along the long bone toward a corresponding other of the distal end and the proximal end, the intramedullary nail having a first end, a second end and an elongate shank extending along a central longitudinal axis and having a longitudinal length between the first end and the second end of the intramedullary nail for locating the first end adjacent the corresponding other of the distal end and the proximal end of the long bone when the second end is placed at the one of the proximal end and the distal end of the long bone; at least one socket extending transversely into the shank intermediate the first and second ends of the intramedullary nail, the socket being spaced away from each of the first and second ends a distance sufficient to assure that the socket is juxtaposed with the bone shaft upon insertion of the intramedullary nail into the long bone; at least one anchoring pin for being secured within the socket to extend transversely from the shaft of the long bone; a drill guide having at least one drill guide passage for alignment with the fracture; and a coupling arrangement for coupling the drill guide with the anchoring pin, such that the drill guide passage is aligned with the fracture for guiding a drill to the fracture and creating a hole in the long bone for the subsequent insertion of a stabilizing fastener to stabilize the fracture.

In addition, the present invention provides bone fracture treatment method for stabilizing a fracture in a long bone of the body, the long bone having a proximal end, a distal end and a bone shaft extending between the proximal end and the distal end, the fracture being located adjacent one of the distal end and the proximal end, the method comprising: inserting an intramedullary nail in the long bone through one of the proximal end and the distal end to extend longitudinally along the long bone toward a corresponding other of the distal end and the proximal end, the intramedullary nail having a first end, a second end and an elongate shank extending along a central longitudinal axis and having a longitudinal length between the first end and the second end of the intramedullary nail to locate the first end adjacent the corresponding other of the distal end and the proximal end of the long bone when the second end is placed at the one of the proximal end and the distal end of the long bone; the intramedullary nail including at least one socket extending transversely into the shank intermediate the first and second ends of the intramedullary nail, the socket being spaced away from each of the first and second ends a distance sufficient to juxtapose the socket with the bone shaft upon insertion of the intramedullary nail in the long bone; securing an anchoring pin within the one socket such that the anchoring pin extends transversely from the bone shaft of the long bone; coupling a drill guide with the anchoring pin such that a drill guide passage in the drill guide is aligned with the fracture for guiding a drill to the fracture; extending a drill through the drill guide passage and into the long bone to create a hole in the long bone, aligned with the fracture; and inserting a stabilizing fastener into the hole to stabilize the fracture.

The invention will be understood more fully, while still further objects and advantages will become apparent, in the following detailed description of preferred embodiments of the invention illustrated in the accompanying drawing, in which:

FIGS. 6 through 9 are diagrammatic illustrations showing a procedure conducted in accordance with the present invention;

Figure 1:
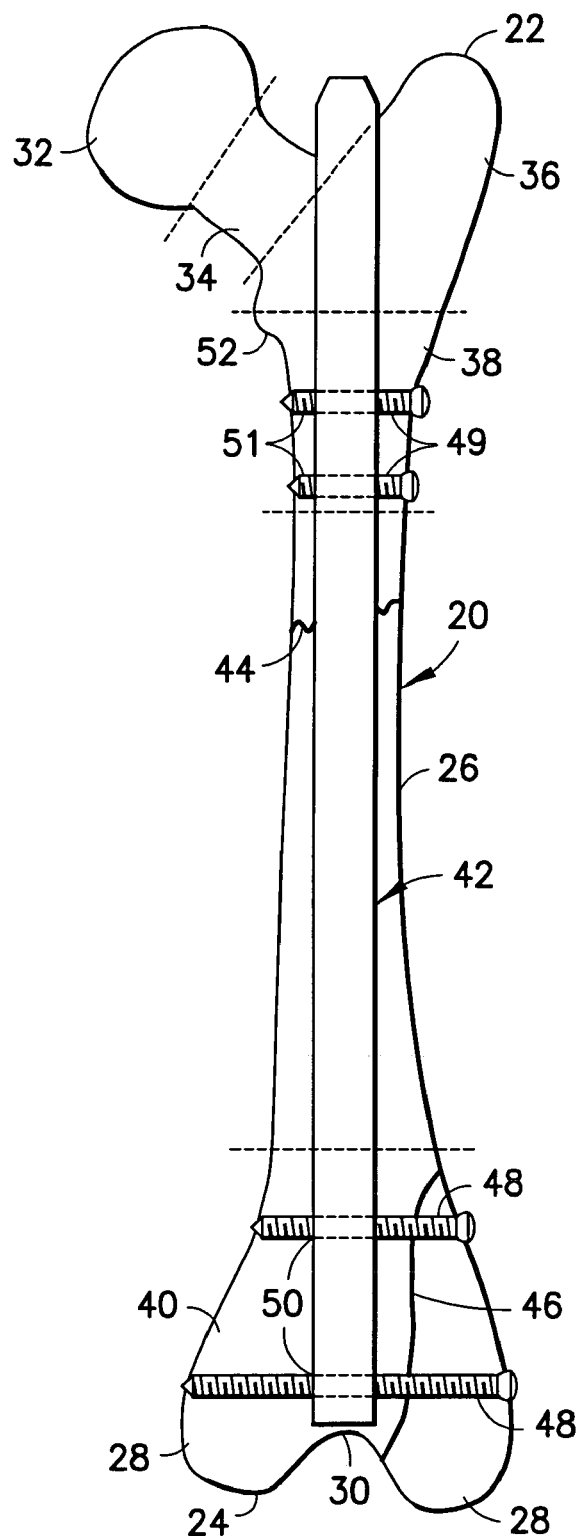
FIG. 1 is a diagrammatic illustration of a long bone in the form of a femur and demonstrating current practice in the treatment of certain fractures in the femur.

Referring now to the drawing, and especially to FIG. 1 thereof, a long bone of the body is illustrated in the form of a femur 20 having a proximal end 22, a distal end 24, and a femoral shaft 26 extending longitudinally between the proximal end 22 and the distal end 24. Distal end 24 includes condyles 28 and an intercondylar notch 30. For purposes of the present description, the portion of the femur 20 adjacent the proximal end 22 is divided into regions, identified herein as femoral head 32, femoral neck 34, intertrochanteric region 36 and subtrochanteric region 38. A supracondylar region 40 is identified adjacent the distal end 24 of femur 20.

Current practice includes the management of certain fractures of the femoral shaft 26 and in the supracondylar region 40 of the femur 20 through the use of intramedullary nails in the form of retrograde nails inserted through a relatively small incision at the knee. Thus, as shown in FIG. 1, an intramedullary nail in the form of a conventional retrograde nail 42 has been inserted longitudinally into the femur 20 through intercondylar notch 30 and has been advanced into the femoral shaft 26. A fracture 44 in the femoral shaft 26 and a fracture 46 in the supracondylar region 40 are stabilized by fixation screws 48 and 49 extending through retrograde nail 42 at 50 and 51, respectively. Retrograde nails, such as that illustrated by retrograde nail 42, ordinarily are not extended beyond the lesser trochanter 52, shown in the vicinity of subtrochanteric region 38, and always have been confined to treatment of fractures in the femoral shaft 26 or the supracondylar region 40, as shown in FIG. 1. Because the insertion of a retrograde nail requires only a relatively small incision, usually no more than one to two inches long, and no muscular dissection, blood loss is minimal and recovery is accelerated. These retrograde nails are used in conjunction with locking screws, such as fixation screws 48, which are inserted percutaneously and require incisions of one centimeter or less, thereby further minimizing blood loss and reducing recovery time. Moreover, intercondylar notch 30 is accessed readily for the insertion of a retrograde nail, rendering the use of retrograde nails simple and effective.

Figure 2:
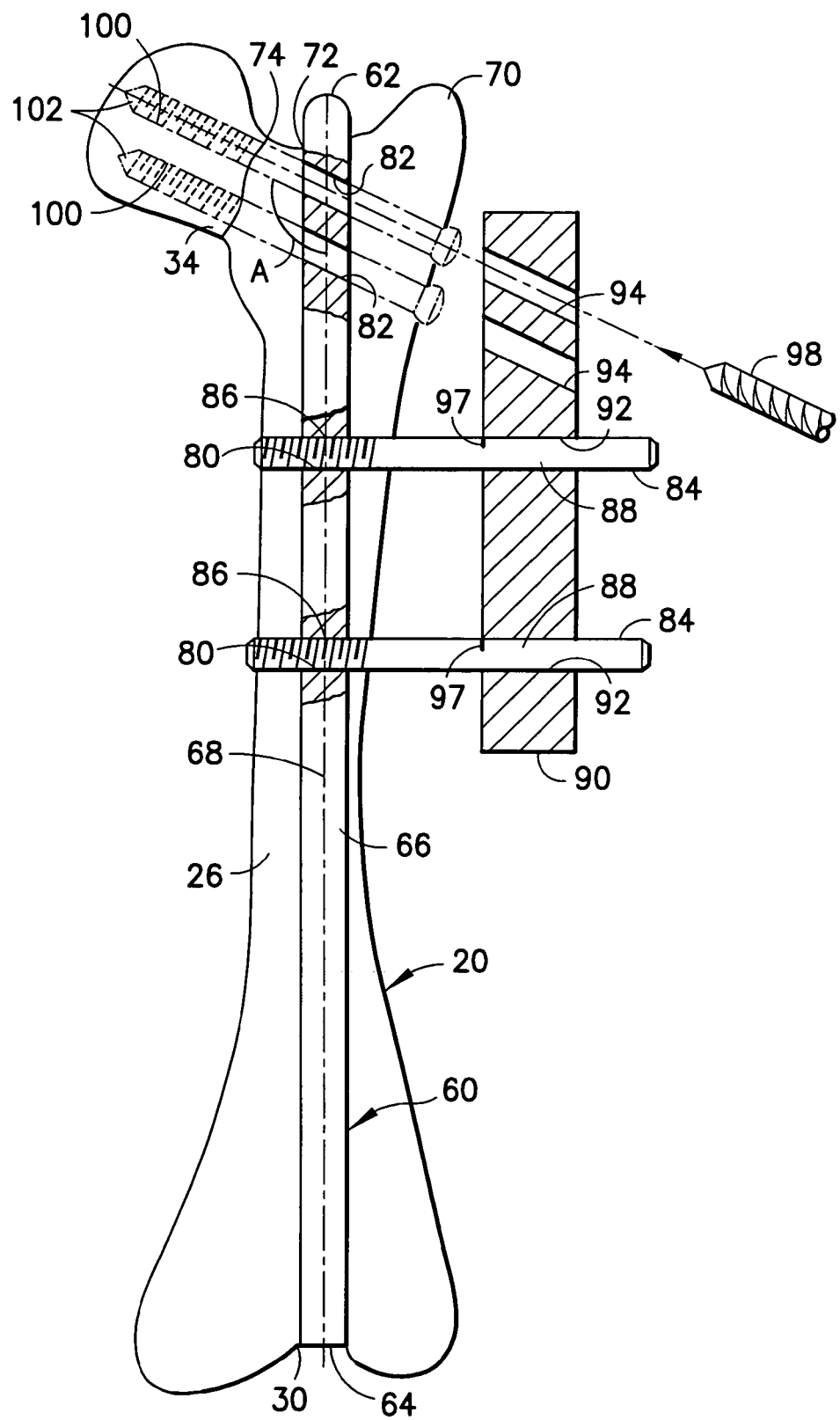
FIG. 2 is a diagrammatic illustration showing components of the present invention in place within and on the femur.

The embodiment of the present invention illustrated in FIG. 2 treats fractures adjacent the proximal end of a long bone through the use of an intramedullary nail in the form of a retrograde nail of extended length. Thus, a retrograde nail 60 includes a first end 62, a second end 64 and an elongate shank 66 extending between the first and second ends 62 and 64 along a central longitudinal axis 68, the shank 66 being long enough so that the first end 62 is extended beyond the femoral shaft 26 of femur 20 and into the trochanteric area 70. In the illustrated embodiment, first end 62 extends beyond the trochanteric area 70, penetrating the pyriformis fossa 72, to treat a fracture 74 in the femoral neck 34. Retrograde nail 60 is inserted at intercondylar notch 30 so that the advantages of ready access, minimal blood loss and accelerated recovery are realized.

In order to stabilize the fracture 74, shank 66 of retrograde nail 60 is provided with precisely located sockets 80, extending transversely into shank 66, preferably normal to axis 68, intermediate the ends 62 and 64 of the retrograde nail 60, and precisely located further passages in the form of holes 82, placed adjacent the first end 62 and extending through the shank 66 at an obtuse angle A to axis 68, for purposes to be described in detail below. Once retrograde nail 60 is in place, anchoring pins 84 are secured within corresponding sockets 80, as by threaded connections at 86, and provide outward extensions 88. The location of the anchoring pins 84 intermediate the ends 62 and 64 of retrograde nail 60, spaced longitudinally away from the proximal and distal regions of the femur 20, places the anchoring pins 84 at locations along femoral shaft 26 where the anchoring pins 84 need penetrate only a minimal amount of soft tissue, thereby minimizing blood loss and realizing concomitant benefits. Moreover, the intermediate location of sockets 80 enables ease of locating of the sockets 80 for insertion of anchoring pins 84. Further, the intermediate location of sockets 80 and anchoring pins 84 provides unrestricted access to the proximal regions of the femur 20, as well as to the distal regions, for the stabilization of fractures in these regions.

Once anchoring pins 84 are in place, a drill guide 90 is coupled to the anchoring pins 84. To this end, drill guide 90 is provided with a coupling arrangement shown in the form of precisely located bores 92 complementary to anchoring pins 84 so that drill guide 90 is slipped over anchoring pins 84 and placed adjacent femur 20. Drill guide 90 includes drill guide passages 94 which extend through a drill block 96 at obtuse angle A to axis 68 and which are aligned with holes 82 in shank 66 of retrograde nail 60 when the drill guide 90 is placed appropriately on anchoring pins 84, as indicated by registration of the drill guide 90 with index marks 97 placed on the anchoring pins 84. In general, angle A is within a range of up to about 150°. A drill 98 then is guided through drill guide passages 94 and into femoral neck 34 to drill holes 100 for the subsequent reception of stabilizing fasteners, shown in the form of fixation screws 102, which bridge the fracture 74 to stabilize the fracture 74. Thus, subsequent to the drilling of holes 100 by drill 98, fixation screws 102 each are inserted in a precisely determined location and orientation with a minimal invasion of soft tissue.

Figure 3:
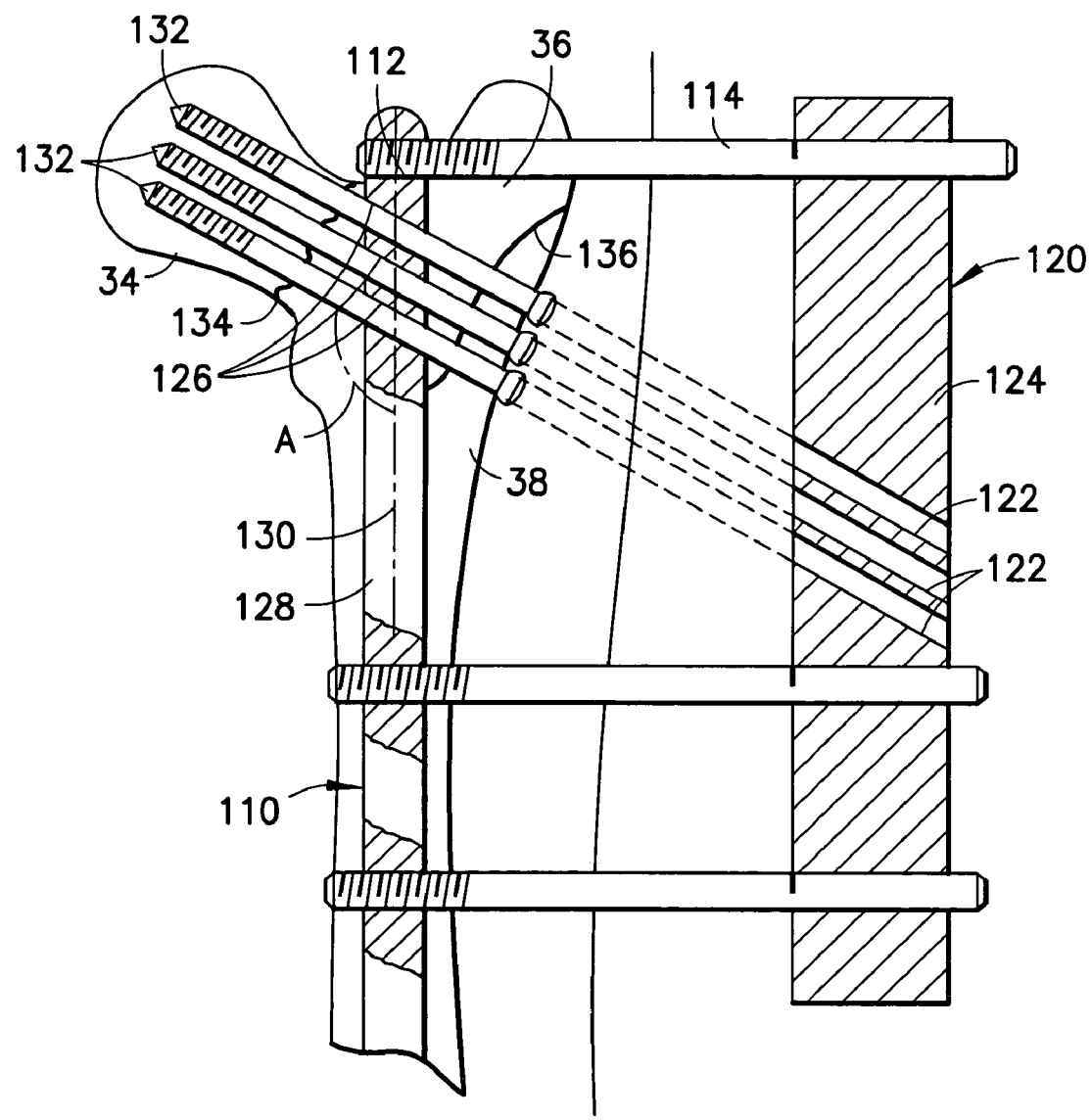
FIG. 3 is a diagrammatic illustration similar to a portion of FIG. 2 and showing alternate components.

Turning now to FIG. 3, an alternate retrograde nail 110 includes a third socket 112 for a third anchoring pin 114 which provides additional stability to an alternate drill guide 120 having three drill guide passages 122, each extending through a drill block 124 at obtuse angle A. The guide passages 122 are aligned with three further passages in the form of holes 126 which pass through shank 128 of the retrograde nail 110, each at obtuse angle A to the central longitudinal axis 130 of the shank 128. In this manner, three stabilizing fasteners, shown in the form of fixation screws 132, stabilize a fracture 134 in the femoral neck 34. The same arrangement is effective in treating a fracture 136 in the intertrochanteric region 36, and a similar arrangement may be made available for treating a fracture (not shown) in the subtrochanteric region 38.

Figure 4:
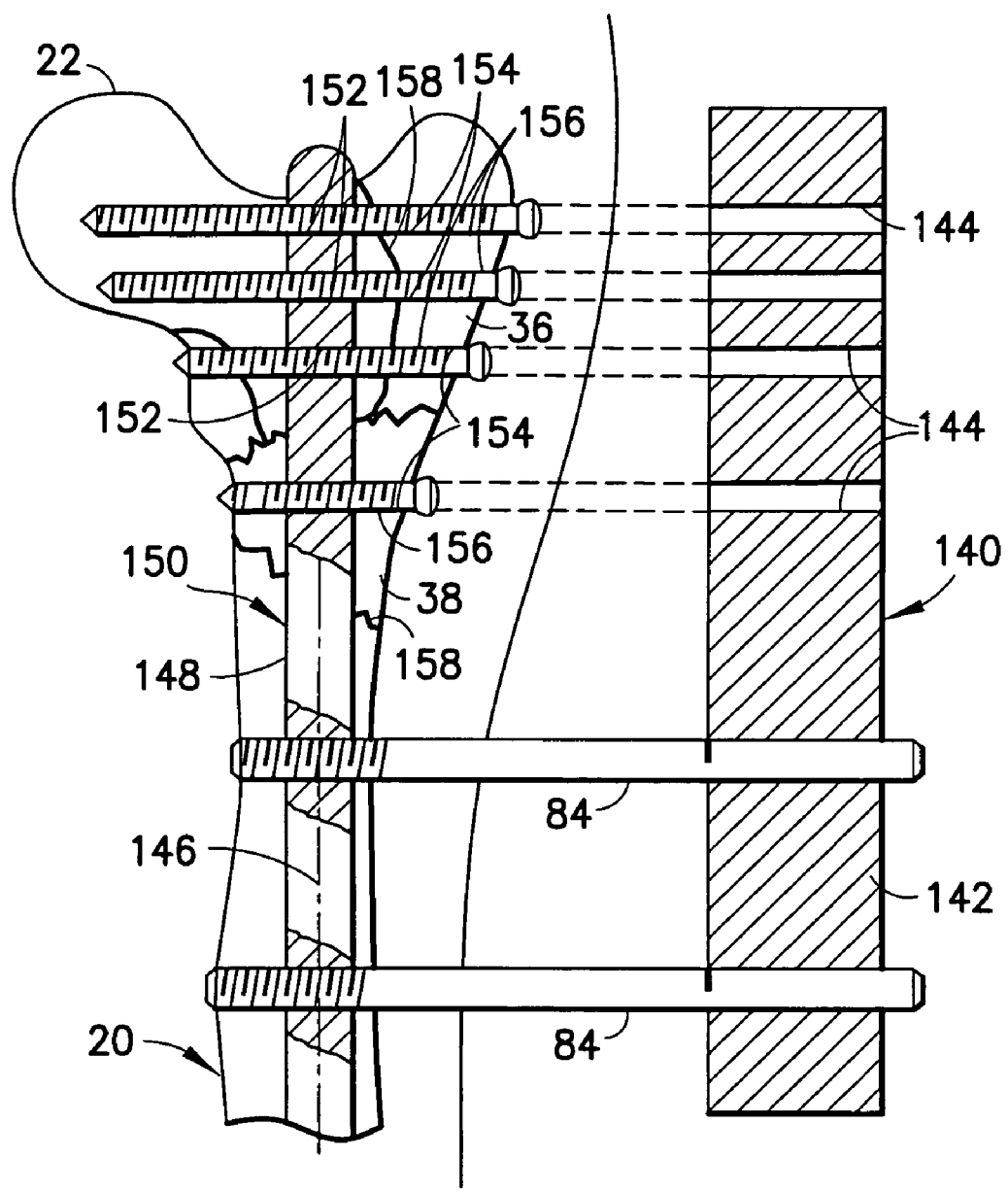
FIG. 4 is a diagrammatic illustration similar to FIG. 3 and showing further alternate components.

In the embodiment illustrated in FIG. 4, an alternate drill guide 140 includes a drill block 142 with multiple drill guide passages 144 extending in a direction essentially normal to the central longitudinal axis 146 of the shank 148 of an alternate retrograde nail 150. The drill guide passages 144 are aligned with corresponding further passages in the form of holes 152 extending through shank 148, essentially normal to axis 146, and multiple holes 154 are drilled to accommodate multiple stabilizing fasteners, shown in the form of fixation screws 156, for stabilizing fractures adjacent the proximal end 22 of femur 20. In the illustrated arrangement, fixation screws 156 are effective to stabilize fractures in the intertrochanteric region 36 and in the subtrochanteric region 38, the fractures being illustrated at 158. Here again, the coupling of the drill guide 140 with anchoring pins 84 located along the portion of shank 148 intermediate the ends of the shank 148 enables a minimally invasive procedure for the treatment of femoral hip fractures.

Figure 5:
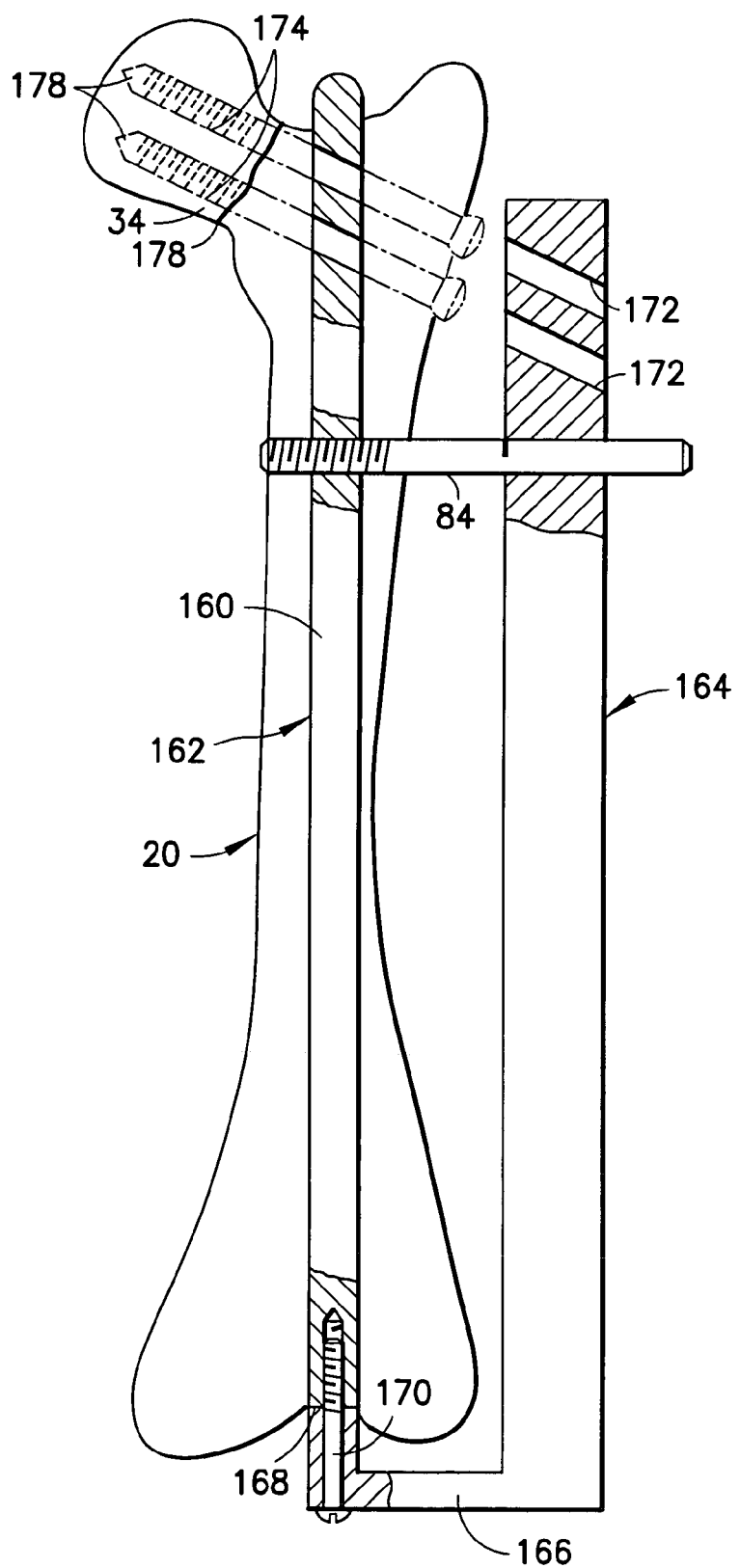
FIG. 5 is a diagrammatic illustration similar to FIG. 2 and showing another alternate arrangement.

In the embodiment illustrated in FIG. 5, a single anchoring pin 84 is secured to the shank 160 of an alternate retrograde nail 162 and locates a drill guide 164 having a support arm 166 affixed to the distal end 168 of the shank 160 by a threaded fastener 170. In this manner, the drill guide 164 is accurately located and secured in place with a minimal number of relatively small incisions. Drill passages 172 are located for drilling holes 174 which receive fixation screws 176 to stabilize a fracture 178 in the femoral neck 34 of femur 20.

Referring now to FIGS. 6 through 9, the procedure by which a retrograde nail constructed in accordance with the present invention is inserted into femur 20 is shown diagrammatically. Initially, access to the distal end 24 of the femur 20 is gained by a one to two inch incision over the patellar tendon, and the tendon is either split or is retracted laterally to expose the intercondylar notch 30. A guide wire 190 is attached to a drill 192, is inserted into the intercondylar notch 30, under image intensification, and is advanced into the distal femoral canal 194, as illustrated in FIG. 6. Subsequently, a cannulated drill 196 is slipped over the guide wire 190 and is advanced to create an entry hole 198 in the distal end 24 of the femur 20. Preferably, the entry hole 198 has a diameter of about 12 to 14 mm. The guide wire 190 and the drill 196 then are removed.

A sturdier guide wire 200 then is introduced through entry hole 198 and, as seen in FIG. 7, is advanced within the femoral canal 194, the guide wire 200 being provided with a sharp tip 202 to facilitate advancement into the trochanteric area 204. Depending upon the length and configuration of the retrograde nail to be inserted, the guide wire 200 optionally may be driven through the junction 205 of the femoral neck 34 and the greater trochanter 206, and into the pyriformis fossa 208, as indicated in phantom. A motorized flexible cannulated reamer 210 having a cutting tip 212 is employed to open the femoral canal 194 and the reamer 210 is advanced through the trochantric area 204 and, optionally, into the pyriformis fossa 208, guided during advancement by the guide wire 200. Using progressively larger diameter reamers, preferably in diametric increments of 0.5 mm, the femoral canal 194 and, optionally, the junction 205 are reamed to the desired diameter, preferably in the range of about 12 to 14 mm. Then, as shown in FIG. 8, a selected retrograde nail 220 is inserted into the prepared femoral canal 194 of the femur 20. In order to facilitate the insertion, guide wire 200 is replaced with a relatively larger diameter guide wire 222 and retrograde nail 220 is provided with a complementary central longitudinal bore 224 so that retrograde nail 220 is slipped over guide wire 222 and is guided by guide wire 222 through entry hole 198 and along the prepared femoral canal 194. Depending upon the length of retrograde nail 220, the first end 226 of the nail shank 228 is located either at junction 205 or proximally beyond junction 205, as illustrated in phantom.

Once retrograde nail 220 is fully inserted, as seen in FIG. 9, the retrograde nail 220 is locked in place, utilizing two locking screws 230 placed adjacent the second end 232 of the nail shank 228 and passing through the nail shank 228 in a manner now conventional in the use of retrograde nails. Using an image intensifier and a radiolucent drill (not shown), two holes 234 are drilled in the femoral shaft 26 in alignment with sockets 236 in the nail shank 228. The sockets 236 correspond to sockets 80 described above in connection with the embodiment illustrated in FIG. 2 and are located and configured to receive anchoring pins 84 for coupling a drill guide to the retrograde nail 220. As before, sockets 236 are located intermediate the ends of the nail shank 228. Preferably, the sockets are spaced apart by approximately 4 cm. Optionally, a third socket 238 is placed adjacent the first end 226 of the nail shank 228 for the reception of an optional third anchoring pin 114, as described in connection with the embodiment illustrated in FIG. 3.

Figure 10:
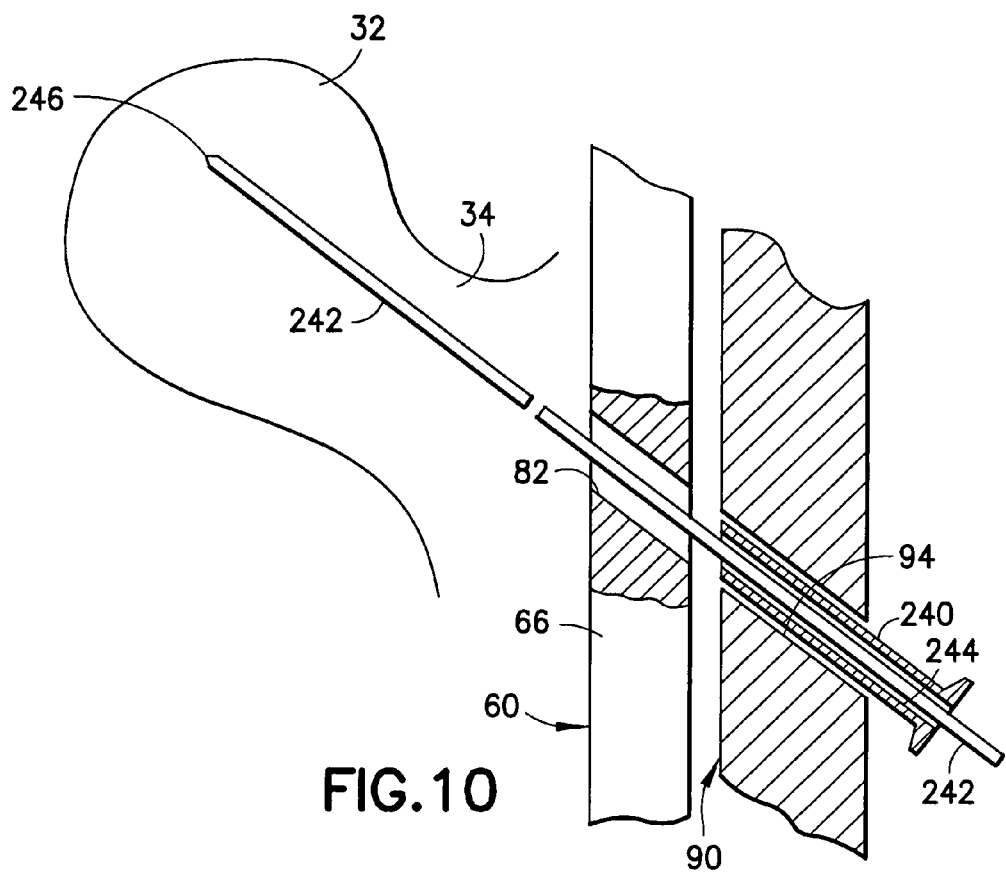
FIGS. 10 and 11 are enlarged, fragmentary diagrammatic illustrations showing steps in a further procedure conducted in accordance with the present invention.
Figure 11:
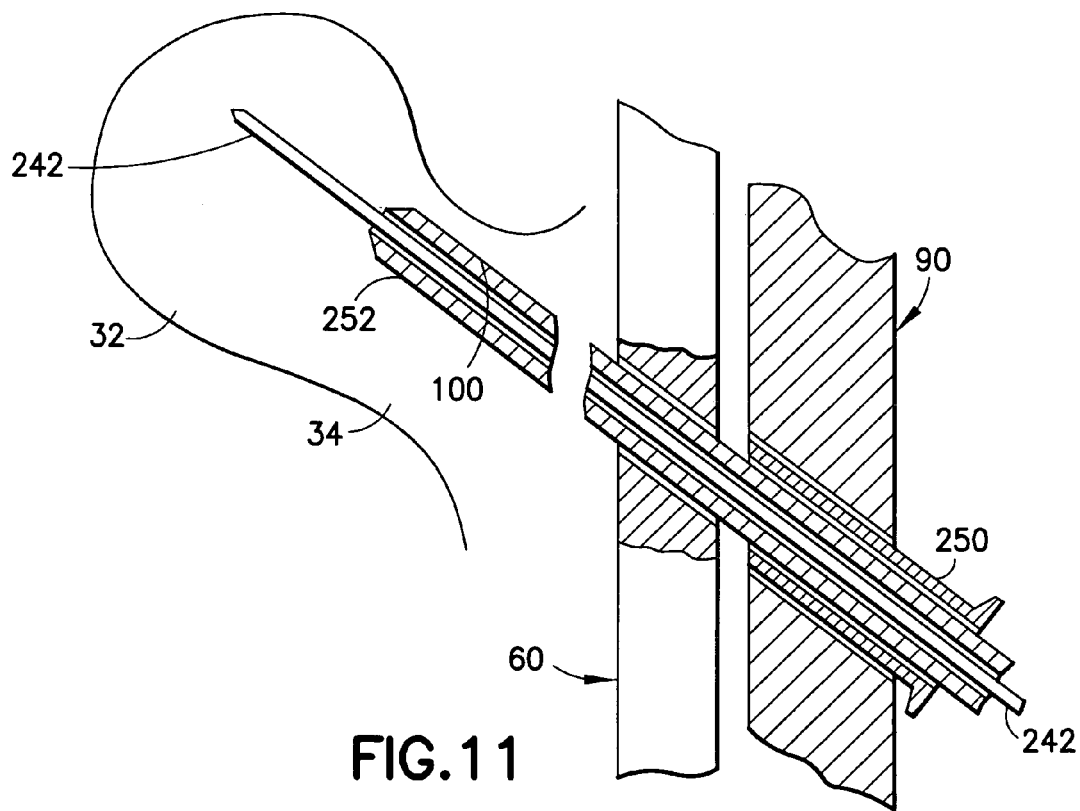

A preferred procedure for drilling holes 100 is illustrated in FIGS. 10 and 11. With drill guide 90 placed in position, as described above in connection with FIG. 2, a guide wire sleeve 240 is seated within a drill guide passage 94. A guide wire 242 has a diameter complementary to the diameter of a bore 244 extending through the guide wire sleeve 240 and bears a sharp point 246. Guide wire 242 is advanced, under power, through hole 82 in the shank 66 of retrograde nail 60 and, guided by bore 244, enters the femoral neck 34 and the femoral head 32. The guide wire sleeve 240 then is removed and replaced with a drill bushing 250, and a cannulated drill 252 is advanced through the drill bushing 250 and guided by the guide wire 240 into the femoral neck 34 and into the femoral head 32 to create hole 100 for the subsequent reception of a fixation screw 102. Guide wire 240 assures accuracy in the placement of a suitable hole 100.

Figure 12:
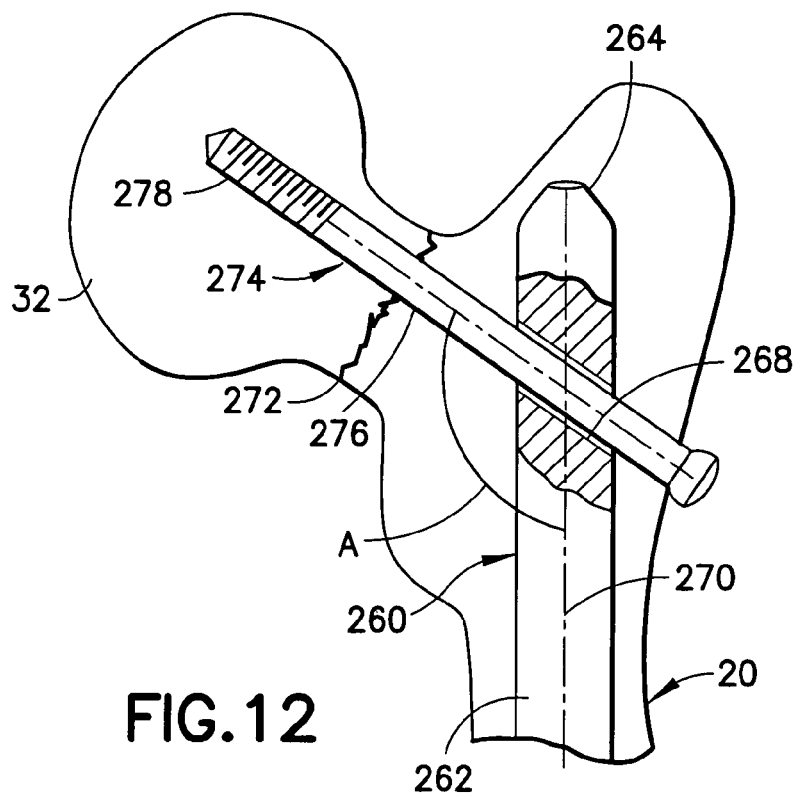
FIG. 12 is an enlarged, fragmentary diagrammatic illustration showing a detail of a fracture in the femur, as stabilized in accordance with the present invention.

Referring now to FIG. 12, a retrograde nail constructed in accordance with the present invention is shown at 260 and includes a shank 262 having a first end 264 and passage in the form of a hole 268 passing through the shank 262 adjacent the first end 264 at an obtuse angle A to the central axis 270 of the shank 262. A fracture 272 at the femoral neck 34 of femur 20 is to be treated by bridging the fracture 272 with fixation screws, one of which screws is illustrated at 274. In the illustrated embodiment, fixation screw 274 has a shank 276 with a diameter complementary to the diameter of hole 268 so that fixation screw 274 is capable of sliding within the hole 268, along the direction making obtuse angle A with axis 270. A relatively smaller diameter threaded portion 278 of fixation screw 274 engages the femoral head 32 and the femoral neck 34 to stabilize the fracture 272.

Figure 13:
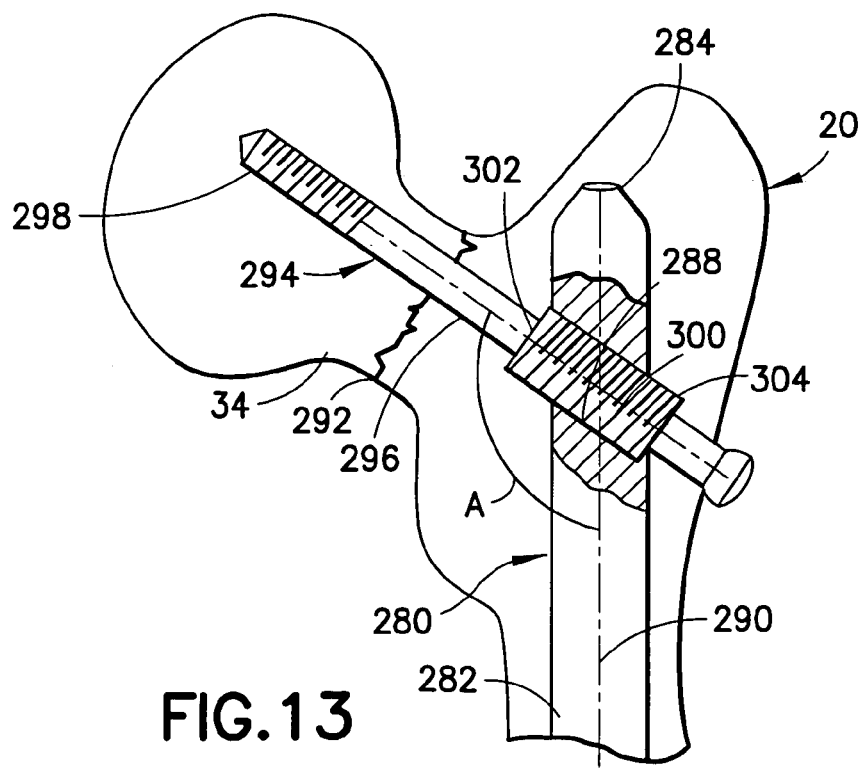
FIG. 13 is an enlarged, fragmentary diagrammatic illustration similar to FIG. 12 and showing an alternate arrangement.

Turning to FIG. 13, another retrograde nail constructed in accordance with the present invention is shown at 280 and includes a shank 282 having a first end 284 and a hole 288 passing through the shank 282 adjacent the first end 284 at an obtuse angle A to the central axis 290 of the shank 282. A fracture 292 at the femoral neck 34 of femur 20 is to be treated by bridging the fracture 292 with fixation screws, one of which screws is illustrated at 294. In the illustrated embodiment, fixation screw 294 has a shank 296 with a diameter smaller than the diameter of hole 288 and a threaded end portion 298 of the fixation screw 294 engages the femoral had 32 and the femoral neck 34 to stabilize the fracture 292. The hole 288 includes an internal screw thread 300 and the shank 296 of fixation screw 294 includes an intermediate portion 302 which bears an external screw thread 304 complementary to internal screw thread 300. The spacing along shank 296 between the end portion 298 of fixation screw 294 and the intermediate portion 302 is such that upon reaching the desired stabilization of fracture 292, fixation screw 294 is locked in place within the hole 288 of the shank 282 of retrograde nail 280, by virtue of the interengaged screw threads 300 and 304, thereby coupling the fixation screw 294 with the shank 282 of the retrograde nail 280 for increased stability.

Figure 14:
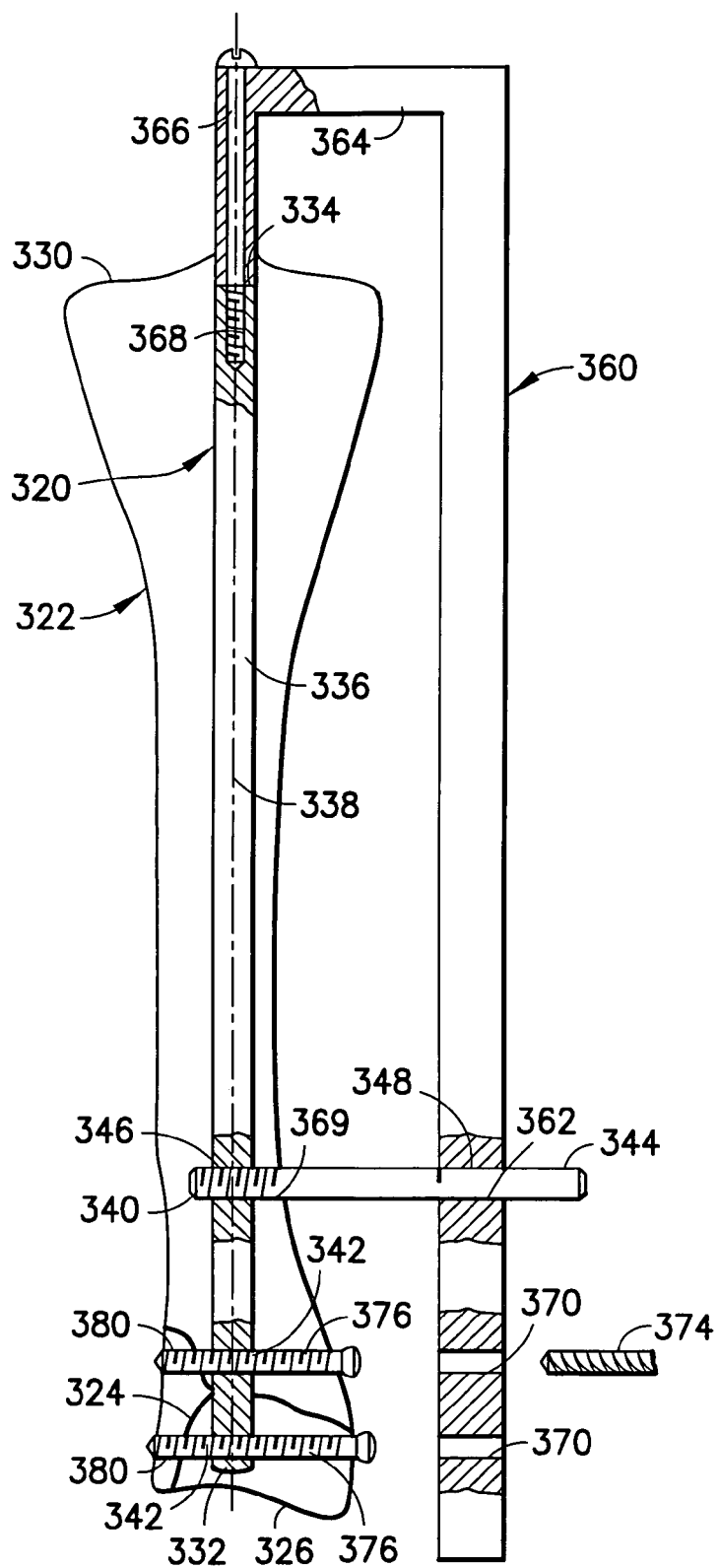
FIG. 14 is a diagrammatic illustration showing alternate components of the present invention in place within and on a tibia.

In the embodiment of the invention illustrated in FIG. 14, an intramedullary nail in the form of an antegrade nail 320 is inserted into a tibia 322 to stabilize a distal tibia fracture 324 adjacent the distal end 326 of the tibia 322. Antegrade nail 320 is inserted at the proximal end 330 of tibia 322 and extends toward the distal end 326. Antegrade nail 320 includes a first end 332, a second end 334 and an elongate shank 336 extending between the first and second ends 332 and 334 along a central longitudinal axis 338, the shank 336 being long enough so that the first end 332 is extended to the fracture 324 to enable treatment of the fracture 324. Antegrade nail 320 is inserted at a location which provides the advantages of ready access, minimal blood loss and accelerated recovery.

In order to stabilize the fracture 324, shank 336 of antegrade nail 320 is provided with at least one precisely located socket 340, extending transversely into shank 336, preferably normal to axis 338, intermediate the ends 332 and 334 of the antegrade nail 320. Precisely located further passages in the form of holes 342, are placed adjacent the first end 332 and extend through the shank 336 for purposes to be described in detail below. Once antegrade nail 320 is in place, an anchoring pin 344 will be secured within socket 340, as by a threaded connection at 346, as described below, and provides an outward extension 348. The location of the anchoring pin 344 intermediate the ends 332 and 334 of antegrade nail 320, spaced longitudinally away from the proximal and distal regions of the tibia 322, places the anchoring pin 344 at a location along tibial shaft 350 where the anchoring pin 344 need penetrate only a minimal amount of soft tissue, thereby minimizing blood loss and realizing concomitant benefits. Moreover, the intermediate location of socket 340 enables ease of locating the socket 340 for insertion of anchoring pin 344. Further, the intermediate location of socket 340 and anchoring pin 344 provides unrestricted access to the distal regions of the tibia 322, as well as to the proximal regions, for the stabilization of fractures in these regions.

A drill guide 360 is provided with a coupling arrangement which includes a precisely located bore 362 complementary to anchoring pin 344. Drill guide 360 is provided with an end support in the form of a bracket 364 which is integral with the drill guide 360 and is affixed to the second end 334 of antegrade nail 320 by means of a threaded fastener 366 engaged with an end socket 368 in the shank 336 of antegrade nail 320. Once antegrade nail 320 is in place, with bracket 364 affixed to second end 334 of the antegrade nail 320, bore 362 is aligned with socket 340, utilizing radiological or another of several available surgical alignment techniques, and is employed to guide a drill 374 for creating a hole 369 aligned with socket 340. Anchoring pin 344 then is inserted through bore 362 and hole 369 to be secured within socket 340 and thereby stabilize the drill guide 360 in place. Drill guide 360 includes drill guide passages 370 which extend through a drill block 372 normal to axis 338 and which are aligned with holes 342 in shank 336 of antegrade nail 320 when the drill guide 360 is placed appropriately on anchoring pin 344 and secured by end bracket 364. A drill 374 then is guided through drill guide passages 370 and into tibia 322 to drill holes 376 for the reception of stabilizing fasteners, shown in the form of fixation screws 380, which bridge the fracture 324 to stabilize the fracture 324. Thus, fixation screws 380 each are inserted in a precisely determined location and orientation with a minimal invasion of soft tissue.

While the above description of preferred embodiments of the invention is directed mainly to fractures of the femur and the tibia, the improvements of the present invention are applicable to many other bone fractures and, in particular, to fractures located in or near joints, such as peri- and intra-articular fractures.

It will be seen that the present invention attains the several objects and advantages summarized above, namely: Provides apparatus and procedure enabling minimally invasive treatment of long bone fractures such as femoral hip fractures with concomitant minimal blood loss, shortened hospital stay and less discomfort, as well as reduced costs; allows the stabilization of long bone fractures, such as femoral hip fractures, without the necessity for excessive dissection of skin and muscle tissue around the hip; accomplishes the stabilization of long bone fractures such as femoral hip fractures with minimal to no radiographic support, enabling effective treatment at less elaborate and less expensive facilities; enables greater precision with increased ease for more effective fixation, especially in treating intertrochanteric and subtrochanteric hip fractures, without the need for major incisions in the hip area; permits the percutaneous fixation of undisplaced femoral neck fractures with diminished failure rates; reduces pain and recovery time; provides a surgeon with better options for treating long bone fractures such as femoral hip fractures.

It is to be understood that the above detailed description of preferred embodiments of the invention are provided by way of example only. Various details of design, construction and procedure may be modified without departing from the true spirit and scope of the invention, as set forth in the appended claims.

The embodiments of the invention in which an exclusive property or privilege is claimed are defined as follows:

1. A bone fracture treatment apparatus for stabilizing a fracture in a long bone of the body, the long bone having a proximal end, a distal end and a bone shaft extending between the proximal end and the distal end, the fracture being located adjacent one of the proximal end and the distal end, the apparatus comprising:

an intramedullary nail insertable in the long bone through one of the proximal end and the distal end to extend longitudinally along the long bone toward a corresponding other of the distal end and the proximal end, the intramedullary nail having a first end, a second end and an elongate shank extending along a central longitudinal axis and having a longitudinal length between the first end and the second end of the intramedullary nail for locating the first end adjacent the corresponding other of the distal end and the proximal end of the long bone when the second end is placed at the one of the proximal end and the distal end of the long bone;

at least one socket extending transversely into the shank intermediate the first and second ends of the intramedullary nail, the socket being spaced away from each of the first and second ends a distance sufficient to assure that upon insertion of the intramedullary nail into the long bone the socket is juxtaposed with the bone shaft and is located adjacent the one of the proximal end the distal end of the long bone;

at least one anchoring pin dimensioned and configured relative to the socket for being secured within the socket, located and secured to the shaft of the intramedullary nail so as to extend transversely from the shaft of the long bone adjacent the one of the proximal end and the distal end of the long bone;

a drill guide having at least one drill guide passage for alignment with the fracture; and a coupling arrangement for coupling the drill guide with the anchoring pin such that upon securing the anchoring pin within the socket and coupling the drill guide with the anchoring pin, the drill guide passage is aligned with the fracture for guiding a drill to the fracture and creating a hole in the long bone for the subsequent insertion of a stabilizing fastener to stabilize the fracture.

2. The apparatus of claim 1 wherein the socket and the anchoring pin include complementary screw threads for securing the anchoring pin within the socket.

3. The apparatus of claim 1 including at least two sockets spaced apart longitudinally from one another and at least two corresponding anchoring pins, and wherein the coupling arrangement is configured for coupling the drill guide to the two anchoring pins.

4. The apparatus of claim 3 wherein each socket and each anchoring pin include complementary screw threads for securing each anchoring pin within a corresponding socket.

5. The apparatus of claim 1 wherein the drill guide passage extends in a direction making an obtuse angle with the central longitudinal axis of the shank.

6. The apparatus of claim 1 wherein the drill guide passage extends in a direction essentially normal to the central longitudinal axis of the shank.

7. The apparatus of claim 1 including at least one further passage, the further passage extending through the shank of the intramedullary nail and being aligned with the drill guide passage when the drill guide is coupled to the anchoring pin.

8. The apparatus of claim 7 wherein the drill guide passage extends in a direction making an obtuse angle with the central longitudinal axis of the shank, and the further passage extends along that direction for alignment with the drill guide passage when the drill guide is coupled to the anchoring pin.

9. The apparatus of claim 7 wherein the drill guide passage extends in a direction extending essentially normal to the central longitudinal axis of the shank, and the further passage extends along that direction for alignment with the drill guide passage when the drill guide is coupled to the anchoring pin.

10. The apparatus of claim 7 wherein the further passage includes an internal screw thread for engaging a complementary external screw thread on the stabilizing fastener to lock the stabilizing fastener in place when the stabilizing fastener is in place to stabilize the fracture.

11. The apparatus of claim 1 wherein the coupling arrangement includes an end support for coupling the drill guide to one of the first and second ends of the shank of the intramedullary nail.

12. A bone fracture treatment method for stabilizing a fracture in a long bone of the body, the long bone having a proximal end, a distal end and a bone shaft extending between the proximal end and the distal end, the fracture being located adjacent one of the distal end and the proximal end, the method comprising:

inserting an intramedullary nail in the long bone through one of the proximal end and the distal end to extend longitudinally along the long bone toward a corresponding other of the distal end and the proximal end, the intramedullary nail having a first end, a second end and an elongate shank extending along a central longitudinal axis and having a longitudinal length between the first end and the second end of the intramedullary nail to locate the first end adjacent the corresponding other of the distal end and the proximal end of the long bone when the second end is placed at the one of the proximal end and the distal end of the long bone;

the intramedullary nail including at least one socket extending transversely into the shank intermediate the first and second ends of the intramedullary nail, the socket being spaced away from each of the first and second ends a distance sufficient to juxtapose the socket with the bone shaft upon insertion of the intramedullary nail in the long bone;

securing an anchoring pin within the one socket such that the anchoring pin extends transversely from the bone shaft of the long bone;

coupling a drill guide with the anchoring pin such that a drill guide passage in the drill guide is aligned with the fracture for guiding a drill to the fracture;

extending a drill through the drill guide passage and into the long bone to create a hole in the long bone, aligned with the fracture; and inserting a stabilizing fastener into the hole to stabilize the fracture.

13. The method of claim 12 wherein the intramedullary nail includes at least two sockets and the method includes securing an anchoring pin within each of the two sockets, and coupling the drill guide with each anchoring pin.

14. The method of claim 12 wherein the intramedullary nail includes at least one further passage, the further passage extending through the shank of the intramedullary nail, the method including aligning the further passage with the drill guide passage when the drill guide is coupled to the anchoring pin such that upon insertion of the stabilizing fastener, the stabilizing fastener is passed through the further passage.

15. The method of claim 14 including locking the stabilizing fastener within the further passage of the shank subsequent to stabilizing the fracture with the stabilizing fastener.

16. The method of claim 12 wherein the intramedullary nail comprises a retrograde nail inserted through the distal end to extend toward the proximal end.

17. The method of claim 12 wherein the intramedullary nail comprises an antegrade nail inserted through the proximal end to extend toward the distal end.

* * * * *